United States Patent
Merckle et al.

(10) Patent No.: US 10,463,761 B2
(45) Date of Patent: Nov. 5, 2019

(54) TISSUE FUSION AGENT

(71) Applicant: Aesculap AG, Tuttlingen (DE)

(72) Inventors: Christof Merckle, Mannheim (DE); Erich Odermatt, Schaffhausen (CH)

(73) Assignee: Aesculap AG, Tuttlingen (DE)

( * ) Notice: Subject to any disclaimer, the term of this patent is extended or adjusted under 35 U.S.C. 154(b) by 695 days.

(21) Appl. No.: 14/765,580

(22) PCT Filed: Mar. 5, 2014

(86) PCT No.: PCT/EP2014/054225
§ 371 (c)(1),
(2) Date: Aug. 4, 2015

(87) PCT Pub. No.: WO2014/135571
PCT Pub. Date: Sep. 12, 2014

(65) Prior Publication Data
US 2015/0367026 A1    Dec. 24, 2015

(30) Foreign Application Priority Data
Mar. 8, 2013  (DE) .................. 10 2013 203 999

(51) Int. Cl.
A61L 27/18    (2006.01)
A61L 27/24    (2006.01)
A61L 27/54    (2006.01)
A61B 18/12    (2006.01)

(52) U.S. Cl.
CPC ............ *A61L 27/18* (2013.01); *A61B 18/12* (2013.01); *A61L 27/24* (2013.01); *A61L 27/54* (2013.01); *A61L 2300/60* (2013.01); *Y10T 428/23943* (2015.04)

(58) Field of Classification Search
CPC .......... A61L 27/18; A61L 27/24; A61L 27/54; A61L 24/001; A61L 24/0015; A61L 24/0042
See application file for complete search history.

(56) References Cited

U.S. PATENT DOCUMENTS

| 6,183,498 | B1 | 2/2001 | Devore et al. |
| 2002/0037323 | A1 | 3/2002 | Prasch et al. |
| 2002/0049503 | A1 | 4/2002 | Milbocker |
| 2004/0266000 | A1 | 12/2004 | Offermann et al. |
| 2005/0129733 | A1 | 6/2005 | Milbocker et al. |
| 2005/0284809 | A1 | 12/2005 | Looney et al. |

FOREIGN PATENT DOCUMENTS

| DE | 10 2009 002 768 A1 | 11/2010 |
| EP | 2 153 791 A1 | 2/2010 |
| EP | 2 567 714 A1 | 3/2013 |
| WO | 00/24436 | 5/2000 |
| WO | 2010/125146 | 11/2010 |
| WO | 2011/138247 | 11/2011 |
| WO | 2011/138347 A2 | 11/2011 |

OTHER PUBLICATIONS

Third Office Action dated Oct. 26, 2017, of corresponding Chinese Application No. 201480013094.4 along with an English translation.
First Examination Report dated Apr. 19, 2018, of corresponding European Application No. 14 707 819.0.
Chinese Office Action dated Nov. 2, 2016, of corresponding Chinese Application No. 201480013094.4, along with an English translation.
English abstract of "Management of idiopathic anal fistula using collagen N/A," Aug. 13, 2008, http://isrctn.org/ISRCTN67277406.

*Primary Examiner* — Zohreh A Fay
(74) *Attorney, Agent, or Firm* — Lewis Kohn & Walker LLP; David M. Kohn

(57) ABSTRACT

A tissue fusion agent includes a particulate and/or fibrous flock material, wherein the fibrous flock material includes monofilament flock fibers and has a fiber length of 100 μm to 3 mm. A discharge device can contain the tissue fusion agent and a surgical system can includes the tissue fusion agent or the discharge device and a tissue fusion instrument.

16 Claims, No Drawings

TISSUE FUSION AGENT

TECHNICAL FIELD

This disclosure relates to a tissue fusion agent, to a discharge device and to a surgical system.

BACKGROUND

Tissue fusion (tissue connection), especially in the form of anastomoses and ligations (ligatures), can be carried out by various techniques, for example, suturing techniques and stapling techniques.

Newer tissue fusion techniques provide for the use of ultrasound, laser irradiation, or heat. Although carrying out those techniques brings about tissue fusion which is reliable and safe from a medical point of view, the disadvantage is that part of the tissue in the fusion region always also becomes degenerated because of the energy input. In some circumstances, this can have an adverse effect on the strength and tightness of the fused tissue.

WO 2011/138347 A2 discloses a surgical system for electrosurgical tissue fusion comprising not only a surgical instrument having two high-frequency current electrodes (HF electrodes), but also a medically compatible material supporting the tissue connection. The material can be, in particular, a collagen disc.

The use of a biocompatible material layer as intermediate layer between body tissue surfaces to be fused is disclosed in DE 10 2009 002 768 A1.

A fundamental disadvantage of the known tissue fusion materials is the application thereof into a tissue region to be fused, that application being very complicated in some cases. A further difficulty is that of achieving a most uniform distribution of the materials in a tissue region to be fused. Moreover, a possible result of inhomogeneities with regard to the material thickness is that the material contracts with great variation upon input of energy. Hence, there is the risk of there being insufficient material provided for strong and tight tissue fusion.

SUMMARY

We provide a tissue fusion agent including a particulate and/or fibrous flock material.

We also provide a discharge device containing the tissue fusion agent including a particulate and/or fibrous flock material.

We further provide a surgical system including the tissue fusion agent including a particulate and/or fibrous flock material and a tissue fusion instrument, the instrument including at least two electrodes that release or take up current or high-frequency current (HF current).

We further yet provide a surgical system including the discharge device containing the tissue fusion agent including a particulate and/or fibrous flock material and a tissue fusion instrument, the instrument including at least two electrodes that release or take up current or high-frequency current (HF current).

DETAILED DESCRIPTION

We provide a tissue fusion agent, i.e., an agent for use in the fusion or connection or the closure of tissue, generally body tissue. The tissue fusion agent is notable, in particular, for the fact that it comprises a particulate and/or fibrous flock material. Alternatively, the tissue fusion agent can comprise a solution, dispersion, suspension or paste which contains the particulate and/or fibrous flock material or is produced using the particulate and/or fibrous flock material.

We surprisingly found that particulate and/or fibrous flock material can be used to some extent as fusion particles and/or fusion fibers to carry out tissue fusion and/or produce medical solutions, dispersions, suspensions or pastes to likewise carry out tissue fusion.

The tissue fusion agent has the following advantages:

Owing to the particulate and/or fibrous design of the flock material, the tissue fusion agent has an enlarged surface area, making it possible to establish improved contact with a tissue region to be fused, the contact being improved in terms of strength and tightness with regard to the fusion to be achieved.

A further advantage associated with the enlarged surface area of the flock material is that generally relatively low amounts of the tissue fusion agent need to be applied into a tissue region to be fused to achieve strong and, in particular, tight, compact and penetrative tissue fusion.

A further advantage of the tissue fusion agent arising from the particulate and/or fibrous design of the flock material is that the tissue fusion agent can be uniformly or homogeneously distributed in a tissue region to be fused, ensuring that there is always sufficient provision of material for strong and, in particular, tight, compact and penetrative tissue fusion.

Any visible inhomogeneities in the distribution of the tissue fusion agent can be easily compensated for by "re-application" of the tissue fusion agent before or during the fusion process.

In addition, it is advantageous that, owing to the particulate and/or fibrous design of the flock material, the tissue fusion agent allows complete coverage of a tissue region to be fused, without complicated adaptations of the tissue fusion agent to the proportions of the tissue region to be fused being required before or during the tissue fusion process.

Apart from that, complete coverage of a tissue region to be fused can ensure, with particular advantage, that the fused tissue parts in a layer arising from the tissue fusion agent after the tissue fusion find sufficient space or pores for cells to grow into.

Also advantageous is the fact that, owing to the particulate and/or fibrous design of the flock material, the tissue fusion agent can be applied in a targeted manner to a tissue region to be fused.

Owing to the particulate and/or fibrous design of the flock material and the associated surface area enlargement, it is additionally possible to more easily and, in particular, more rapidly apply the tissue fusion agent into a tissue region to be fused. Depending on the form of the tissue fusion agent, the latter can be applied as, for example, a dispersion or suspension by spraying (or optionally by spreading) or a paste by brushing to a tissue region to be fused. This likewise contributes to facilitating the performance of tissue fusion.

As a result, the tissue fusion agent can also be applied without relatively great difficulties into poorly accessible treatment areas.

A further advantage is that, owing to the particulate and/or fibrous design of the flock material, the tissue fusion agent can be applied into a tissue region to be fused in reproducible and, in particular, definable amounts, making it altogether possible to carry out the tissue fusion process under reproducible and, in particular, definable conditions.

Through the specific selection of materials and/or additives for the flock material, it is additionally possible to specifically influence or adjust the fusion properties thereof such as, for example, melting ability, adhesiveness and/or conductive or impedance behavior and also resorption properties. This allows not only fusion process-specific but also indication-specific adaptation of the tissue fusion agent. Depending on the material selected, the tissue fusion following performance of the fusion process can be based on a sealing and/or covering film arising from the tissue fusion agent.

The above aspects contribute, with particular advantage, to shortening the fusion process and thus to shortening possible energy input (if the newer tissue fusion techniques mentioned at the start are used), and so the tissue fusion agent altogether also allows the performance of fusion which is more gentle to tissue.

One advantage is that the flock material and thus the tissue fusion agent can be produced in a cost-effective manner. For instance, the flock material can, for example, be extruded and transferred to a particulate and/or fibrous form, for example, by trimming to length, more particularly cutting, or milling.

The term "fibrous flock material" or "flock fibers" means fibers having a defined fiber length (preferred fiber lengths will be mentioned below). The fibrous flock material is usually produced by trimming to length, more particularly cutting, or milling single fibers (such as, for example, extrusion fibers), more particularly so-called continuous fibers.

Preferably, the fibrous flock material is flock fibers, more particularly monofilament flock fibers. Particularly preferably, the fibrous flock material is present in the form of single flock fibers. In other words, it is particularly preferred when the fibrous flock material is not connected, especially not via an adhesive layer, to a substrate, more particularly an implant body and/or a supporting element, or assembled to form a planar structure such as, for example, a non-woven fabric, non-woven scrim, loop-drawingly knitted fabric, loop-formingly knitted fabric or the like.

The fibrous flock material can, in principle, have a fiber length of 40 µm to 15 mm, more particularly 50 µm to 10 mm, preferably 100 µmm to 5.0 mm. The fibrous flock material can, in particular, have a fiber length of 10 µm to 5 mm, more particularly 40 µm to 4 mm, preferably 50 µm to 3 mm, more preferably 100 µm to 2 mm. The fibrous flock material can, with particular preference, have a fiber length of 100 µm to 3 mm, preferably 200 µm to 2 mm.

Furthermore, the fibrous flock material can have a fiber thickness or diameter of 10 µm to 900 µm, more particularly 20 µm to 900 µm, preferably 70 µm to 600 µm, more preferably 100 µm to 400 µm.

In addition, the fibrous flock material can have a linear density of 0.01 dtex to 1000 dtex, more particularly 0.1 dtex to 500 dtex, preferably 0.3 dtex to 200 dtex. The fibrous flock material can, in particular, have a linear density of 0.01 dtex to 100 dtex, preferably 0.1 dtex to 80 dtex, more preferably 0.3 dtex to 40 dtex. The dimension "dtex" (decitex) means a linear density of 1 g per 10 000 m length of the fibrous flock material.

The fibrous flock material can be textured or non-textured. Furthermore, the fibrous flock material can have a circular cross section or a non-circular cross section, more particularly an oval, ellipsoidal, polygonal, for example, triangular, rectangular, square, rhomboidal, pentagonal, hexagonal and/or star-shaped, cross section.

The particulate and/or fibrous flock material can be present in milled form. More particularly, the particulate and/or fibrous flock material can be milled fibers, more particularly milled flock fibers.

The particulate flock material can be present in the form of a powder or granules. The particulate flock material can, in particular, have a particle size or particle diameter of 0.05 µm to 5 mm, more particularly 0.1 µm to 3 mm, preferably 10 µm to 2 mm.

The flock material may comprise a coagulative and/or hot-melt adhesive material or is formed from such a material. More particularly, the flock material comprises a material which is meltable under the influence of high-frequency alternating current (HF current), heat, ultrasound and/or laser radiation or formed from such a material.

Preferably, the flock material comprises a meltable material or formed from such a material which can have a melting point of 40° C. to 120° C., preferably 50° C. to 100° C., depending on the target tissue.

Preferably, the flock material comprises a material which is meltable under the influence of an alternating current having a frequency of 200 kHz to 4000 kHz, more particularly 100 kHz to 600 kHz, preferably 250 kHz to 500 kHz, or formed from such a material.

Particularly preferably, the flock material comprises a resorbable material or is formed from such a material. The surface area enlargement associated with the particulate and/or fibrous design of the flock material favors, with particular advantage, rapid resorption of the tissue fusion agent after tissue fusion has been performed. Moreover, gradual resorption of the tissue fusion agent (after the tissue fusion) ensures that cells, extracellular matrix or tissue completely grow through fused tissue parts. Preferably, fused tissue regions exhibit, as a result of a melting process within the first three to four days after completion of the fusion process, a higher "fusion strength" than in performing tissue fusion in the absence of our tissue fusion agent.

The material described for the flock material can be of synthetic, biological and/or recombinant origin. More particularly, the material for the flock material can be of animal and/or plant origin. As an alternative or in addition, the material for the flock material can be of natural or native origin. The material can, in particular, be of xenogeneic origin, preferably porcine, bovine and/or equine origin. As an alternative or in addition, the material for the flock material can be of human origin. Preferably, the flock material is present as milled flock material.

Preferably, the material for the flock material is a polymer selected in particular from the group comprising synthetic polymer, recombinant polymer, naturally occurring polymer or biopolymer and mixtures, more particularly blends, thereof. Furthermore, the polymer can be a copolymer. The expression "copolymer" means a polymer composed of at least two different monomer units. Thus, the expression "copolymer" encompasses not only copolymers in the narrower sense, i.e., so-called bipolymers (polymers composed of two different monomer units), but also terpolymers, tetrapolymers and the like. The copolymer can additionally be selected from the group comprising random copolymer, alternating copolymer, block copolymer or segmented copolymer, graft copolymer and mixtures, more particularly blends, thereof.

Preferably, the flock material comprises a resorbable material or is formed from such a material selected from the group comprising polyhydroxyalkanoates, proteins, extracellular proteins, serum proteins, polysaccharides, mucopolysaccharides, carboxyl group-bearing polysaccharides, amino group-bearing polysaccharides, aldehyde group-bearing polysaccharides, copolymers thereof, salts thereof, stereoisomers, more particularly diastereomers, thereof and mixtures, more particularly blends, thereof.

More particularly, the flock material can comprise a resorbable material or can be formed from such a material which is selected from the group comprising polyglycolide or polyglycolic acid, polylactide or polylactic acid, polydioxanone, poly-3-hydroxybutyrate or poly-3-hydroxybutyric acid, poly-4-hydroxybutyrate or poly-4-hydroxybutyric acid, polytrimethylene carbonate, poly-ε-caprolactone, polyvinyl alcohol, cotton, cellulose, cellulose derivatives such as, for example, alkylcelluloses, methylcellulose, hydroxyalkylcelluloses, hydroxymethylcellulose, hydroxyethylcellulose, hydroxypropylcellulose, carboxyalkylcelluloses, carboxymethylcellulose, starch, amylose, amylopectin, dextran, dextrin, chitin, chitosan, hyaluronic acid, dextran sulphate, heparin, heparan sulphate, chondroitin sulphate, dermatan sulphate, collagen, gelatin, elastin, reticulin, fibronectin, laminin, fibrin, fibrinogen, albumin, copolymers thereof, salts thereof, stereoisomers, more particularly diastereomers, thereof and mixtures, more particularly blends, thereof.

The flock material may comprise a polyethylene glycol or is formed from a polyethylene glycol. The flock material can comprise a material having a melting point below 100° C., in particular having a melting point of 70° C. to 90° C., or can be formed of such a material.

The flock material can be additized, i.e., comprise one or optionally more additives. To achieve an increase in conductivity or decrease in impedance, it can be provided that the flock material comprises a conductivity-increasing or impedance-decreasing additive, preferably in the form of a salt. The conductivity-increasing or impedance-decreasing additive is preferably selected from the group comprising alkali metal halide, alkaline earth metal halide, phosphate, alkali metal phosphate, alkaline earth metal phosphate, mixed phosphates thereof and mixtures thereof.

For example, the conductivity-increasing or impedance-decreasing additive can be selected from the group comprising sodium chloride, potassium chloride, barium chloride, magnesium chloride, calcium chloride, sodium phosphate, potassium phosphate, barium phosphate, magnesium phosphate, calcium phosphate, mixed phosphates thereof and mixtures thereof.

The conductivity-increasing or impedance-decreasing additive can comprise a proportion of 0.1% by weight to 25% by weight, more particularly 0.5% by weight to 20% by weight, preferably from 0.8% by weight to 10% by weight, based on the total weight of the flock material.

Alternatively, the flock material can comprise a conductivity-decreasing additive, preferably in the form of a metal, for example, selected from the group comprising aluminum, iron, silver, zinc, magnesium and mixtures, more particularly alloys, thereof.

To achieve a biological, pharmaceutical and/or medical effect, it can be provided alternatively or additionally that the flock material comprises an active ingredient selected from the group comprising biological active ingredient, pharmaceutical active ingredient, medical active ingredient and mixtures thereof.

More particularly, the flock material can comprise an active ingredient selected from the group comprising antimicrobial, more particularly antibiotic, active ingredient, wound healing-promoting active ingredient, disinfecting active ingredient, anti-inflammatory active ingredient, blood coagulation-promoting active ingredient, growth factors, cell-differentiating factors, cell-adhesive factors, cell-recruiting factors, cell receptors, cell-binding factors, cytokines, peptides, structural proteins, extracellular proteins such as, for example, collagen, serum proteins such as, for example, albumin, polysaccharides such as, for example, hyaluronic acid, oligonucleotides, polynucleotides, DNA, RNA, salts thereof, stereoisomers, more particularly diastereomers, thereof and mixtures thereof.

For example, the flock material can comprise an active ingredient selected from the group comprising biguanides, polyhexamethylene biguanide (PHMB), triclosan, chlorhexidine, gentamicin, vitamins, copper, zinc, silver, gold, salts thereof, stereoisomers, more particularly diastereomers, and mixtures thereof.

To increase the stability of the flock material, it can be provided that the flock material is present in crosslinked form. The flock material can be physically and/or chemically crosslinked. Physical crosslinking of the flock material can be achieved, for example, by appropriate irradiation techniques. Chemical crosslinking can generally be realized by appropriate chemical crosslinkers.

For example, the flock material can be crosslinked with a chemical crosslinker selected from the group comprising aldehydes such as, for example, formaldehyde, dialdehydes such as, for example, glutaraldehyde, polyaldehydes such as, for example, dextran aldehyde, carbodiimides, diisocyanates such as, for example, hexamethylene diisocyanate, salts thereof and mixtures thereof.

We further provide that the tissue fusion agent comprises a mixture of different particulate and/or fibrous flock materials. In this case, the flock materials can differ from one another with regard to at least one parameter preferably selected from the group comprising particle size (in a particulate flock material), fiber length (in a fibrous flock material), thickness or diameter, linear density (in a fibrous flock material), material and mixtures thereof. With regard to the parameters listed in this paragraph, full reference is made to the description so far.

Particularly preferably, the tissue fusion agent is present in the form of the particulate and/or fibrous flock material or in the form of a mixture of different particulate and/or fibrous flock materials. In other words, particularly preferably, the tissue fusion agent consists of the particulate and/or fibrous flock material or a mixture of different particulate and/or fibrous flock materials. With regard to further features and advantages of the flock material(s), full reference is made to the description so far.

Advantageously, the tissue fusion agent may be present in a sprayable form.

The solution, dispersion, suspension or paste referred to at the start in connection with the tissue fusion agent additionally may comprise a biocompatible solution agent, dispersion agent, or suspension agent, generally water or an aqueous mixture, and/or a biocompatible carrier substance such as, for example, fats, oils, glycerol or the like.

If the tissue fusion agent comprises a suspension comprising the particulate and/or fibrous flock material or produced using the particulate and/or fibrous flock material, it can be provided that the suspension has a flock material content of 1% by weight to 20% by weight, more particularly 3% by weight to 15% by weight, preferably 5% by weight to 10% by weight, based on the total weight of the suspension.

Preferably, the tissue fusion agent can be present in the form of a solution, dispersion, suspension or paste containing the particulate and/or fibrous flock material. Alternatively, the tissue fusion agent can be present in the form of a solution, dispersion, suspension or paste produced using the particulate and/or fibrous flock material. With regard to further features and advantages of the flock material, full reference is made to the description so far.

Furthermore, the tissue fusion agent can be present in aerosolizable form. For example, it can be provided for the tissue fusion agent together with a propellant to be applied as an aerosol. A suitable propellant can be selected from the group comprising perfluorinated ethers (such as, for example, Desfluran), fluorinated hydrocarbons, more particularly fluorinated hydrocarbons of medium chain length (chain length having from two to five carbon atoms) such as, for example, tetrafluoroethane, hexafluoropropane, heptafluoropropane, decafluorobutane, octafluorocyclobutane, noble gases, nitrogen, oxygen, carbon dioxide, dinitrogen oxide and mixtures thereof.

The tissue fusion agent is preferably a surgical tissue fusion agent. The tissue fusion agent is generally suited to closing, occluding or sealing biological tissue, more particularly human and/or animal tissue. Thus, the tissue fusion agent can in particular act as an occlusion agent.

Particularly preferably, the tissue fusion agent is intended for use in carrying out anastomoses and/or ligations (ligatures). The anastomoses can be, in particular, end-to-end anastomoses, side-to-end anastomoses, end-to-side anastomoses and side-to-side anastomoses. Furthermore, the anastomoses can be selected from the group comprising vascular anastomoses, more particularly blood vessel and/or lymphatic vessel anastomoses, intestinal anastomoses, and nerve anastomoses.

Furthermore, the tissue fusion agent can be intended for closing tissue or for sealing tissue after resections, more particularly after partial resections, for example, in the case of organs. A further preferred application area concerns the use of the tissue fusion agent in carrying out electrosurgical fusion of body tissue.

The tissue fusion agent is present in sterile and, in particular, off-the-shelf form. Sterilization of the tissue fusion agent can, for example, be achieved using ethylene oxide and/or gamma irradiation.

We provide a discharge device containing the tissue fusion agent. The discharge device is preferably designed as a spray device. It is advantageous when the discharge device can be used with the aid of trocars, for example, by extension of the spray head.

The discharge device can, in particular, be intended to discharge an aerosol. In this case, it may be useful for the discharge device to contain a suitable propellant in addition to the tissue fusion agent.

With regard to further features and advantages of the discharge device, especially the tissue fusion agent and/or a possible propellant, full reference is made to the description so far.

Lastly, we provide a surgical system comprising the tissue fusion agent or the discharge device and a tissue fusion instrument. The tissue fusion instrument preferably comprises at least two electrodes to release or take up current, more particularly high-frequency current (HF current). Alternatively, the tissue fusion instrument can be a laser instrument or an instrument that generates ultrasonic waves.

However, the surgical system is preferably an electrosurgical system comprising the tissue fusion agent or the discharge device and at least two electrodes for releasing or taking up current, more particularly high-frequency current (HF current). Preferably, the two electrodes are component of a surgical instrument having two tool elements which are movable relative to one another and which each comprise one of the two electrodes, which, preferably in a convergence position of the tool elements, define a minimum distance from one another, lie opposite one another and face one another. With regard to such a surgical instrument, reference is made to WO 2011/138347 A2 and the full disclosure of which is herein incorporated by reference.

With regard to further features and advantages of the surgical system, especially the tissue fusion agent and/or the discharge device, full reference is made to the description so far. Further features and advantages are revealed by the following description of preferred structures and methods in the form of examples. Individual features can, in each case, be realized on their own or in combination with one another. The preferred structures serve solely to further elucidate this disclosure and provide a better understanding without restricting the disclosure thereto.

EXAMPLES

1. Production of Flock Fibers Composed of poly(ε-caprolactone-co-trimethylene carbonate)

An extrusion device was used to extrude fibers composed of poly(ε-caprolactone-co-trimethylene carbonate). The fibers were subsequently trimmed to flock fibers of 100 μm in length using a precision cutting device. After ethylene oxide sterilization and subsequent drying, the flock fibers composed of poly(ε-caprolactone-co-trimethylene carbonate) thus produced were transferred to a spray device. In this form, the flock fibers were used in a sterile environment.

2. Production of Particulate Flock Material Composed of Collagen

Starting from bovine skin, collagen-containing granules were produced and subsequently finely ground. This gave rise to a collagen-containing flock material having a particle size of 10 μm to 80 μm, depending on the milling operation.

3. Reinforcing a Colorectal End-to-End Anastomosis

The distal and proximal intestinal region of a porcine intestinal section to be anastomized was attached in each case to a circular HF instrument (high-frequency current instrument) by a so-called tobacco-pouch suture. Both the distal and the proximal tobacco-pouch suture were subsequently sprayed with the flock fibers produced in step 1 and composed of poly(ε-caprolactone-co-trimethylene carbonate). Thereafter, the two intestinal regions to be anastomized were joined by moving the two surfaces of the HF instrument to one another and triggering the HF generator.

After completion of the fusion process, the tobacco-pouch suture in the interior of the anastomized intestinal sections was cut and the HF instrument was removed from a proximal longitudinal cut. The fused circular intestinal wall with the cut-out of the tobacco-pouch suture was visible.

4. Sealing and Reinforcing a Side-to-Side Anastomosis

The distal and proximal end of a porcine small-intestine section to be anastomized was flocked in each case using the collagen-containing flock material produced in step 2 and then fused using a linear HF instrument. This led to the surface-applied flock material forming a sealing matrix. Subsequently, the fused small-intestine region was cut.

Through a lateral incision of both small-intestine parts, the two intestinal parts were introduced into the linear arms of the HF instrument, the two arms having been sprayed and covered with the collagen-containing flock material.

To achieve side-to-side anastomosis, the two arms of the HF instrument were brought together and the latter was activated by application of a high-frequency alternating current. The small-intestine tissue fused in this way was visible as a white color. Also visible was flock material which was unmelted in some cases.

The incisions required for the arms of the linear HF instrument were sealed using a lateral HF instrument. To close these incisions, the collagen-containing flock material was likewise used.

The invention claimed is:

1. A tissue fusion agent, wherein the tissue fusion agent is present in the form of a fibrous flock material, wherein the fibrous flock material is not connected to a substrate or assembled to form a planar structure.

2. The tissue fusion agent according to claim 1, wherein the fibrous flock material comprises monofilament flock fibers.

3. The tissue fusion agent according to claim 1, wherein the fibrous flock material has a fiber length of 100 µm to 3 mm.

4. The tissue fusion agent according to claim 1, wherein the fibrous flock material has a linear density of 0.01 dtex to 100 dtex.

5. The tissue fusion agent according to claim 1, wherein the flock material comprises a resorbable material or is formed from such a material.

6. The tissue fusion agent according to claim 5, wherein the material is selected from the group consisting of polyhydroxyalkanoates, polyvinyl alcohol, proteins, extracellular proteins, serum proteins, polysaccharides, mucopolysaccharides, carboxyl group-bearing polysaccharides, amino group-bearing polysaccharides, aldehyde group-bearing polysaccharides, copolymers thereof, salts thereof, stereoisomers, diastereomers thereof, mixtures and blends thereof.

7. The tissue fusion agent according to claim 1, wherein the flock material comprises a conductivity-increasing or impedance-decreasing additive, preferably in the form of a salt.

8. The tissue fusion agent according to claim 7, wherein the additive or salt is selected from the group consisting of alkali metal halide, alkaline earth metal halide, phosphate, alkali metal phosphate, alkaline earth metal phosphate, mixed phosphates and mixtures thereof.

9. The tissue fusion agent according to claim 1, wherein the flock material comprises a conductivity-decreasing additive in the form of a metal.

10. The tissue fusion agent according to claim 1, wherein the flock material comprises an active ingredient selected from the group consisting of biological active ingredient, pharmaceutical active ingredient, medical active ingredient and mixtures thereof.

11. The tissue fusion agent according to claim 1, in the form of a surgical tissue fusion agent for use in carrying out anastomoses and/or ligations and/or closing tissue after resections or partial resections.

12. The tissue fusion agent according to claim 1, for use in carrying out electrosurgical fusion of body tissue.

13. The tissue fusion agent according to claim 1, which is in sterile and off-the-shelf form.

14. A discharge device containing the tissue fusion agent according to claim 1.

15. A surgical system comprising the tissue fusion agent according to claim 1 and a tissue fusion instrument, the instrument comprising at least two electrodes that release or take up current or high-frequency current (HF current).

16. A surgical system comprising the discharge device according to claim 14 and a tissue fusion instrument, the instrument comprising at least two electrodes that release or take up current or high-frequency current (HF current).

* * * * *